US005527952A

United States Patent [19]
Kuroda et al.

[11] Patent Number: 5,527,952
[45] Date of Patent: Jun. 18, 1996

[54] PROCESS FOR PRODUCING ALDEHYDE DERIVATIVES

[75] Inventors: Noritaka Kuroda, Toyono-cho; Tatsuhiko Kaneko, Shimamoto-cho; Kenichi Kashiwa, Kobe, all of Japan

[73] Assignee: Takeda Chemical Industries, Ltd., Osaka, Japan

[21] Appl. No.: 258,930

[22] Filed: Jun. 13, 1994

[30] Foreign Application Priority Data

Jun. 14, 1993 [JP] Japan .................................... 5-142131

[51] Int. Cl.$^6$ ............................ C07C 67/08; C07C 67/00
[52] U.S. Cl. .......................... 560/262; 554/150; 554/126
[58] Field of Search ................................. 560/239, 262; 554/150, 126

[56] References Cited

U.S. PATENT DOCUMENTS 4,175,204  11/1979  Babler .................................. 560/262

FOREIGN PATENT DOCUMENTS 58-198297  11/1993  Japan .
79/00485    7/1979   WIPO .

*Primary Examiner*—José G. Dees
*Assistant Examiner*—Rosalynd A. Williams
*Attorney, Agent, or Firm*—Wenderoth Lind & Ponack

[57] ABSTRACT

The present invention provides a novel process for producing 4-acyloxy-2-methyl-2-buten-1-al readily in high yield from a readily available inexpensive industrial starting compound without using special reaction apparatuses and conditions.

11 Claims, No Drawings

PROCESS FOR PRODUCING ALDEHYDE DERIVATIVES

FIELD OF THE INVENTION

The present invention relates to a novel process for producing aldehyde derivatives, particularly 4-acyloxy-2-methyl-2-buten-1-al. The 4-acyloxy-2-methyl-2-buten-1-al is an important intermediate compound for the production of vitamin A useful as feed additives, medicaments, etc., and is potentially useful as an intermediate compound for the production of other medicaments.

BACKGROUND OF THE INVENTION

The following processes for producing 4-acyloxy-2-methyl-2-buten-1-al, particularly 4-acetoxy-2-methyl-2-buten-1-al have been known.

1)

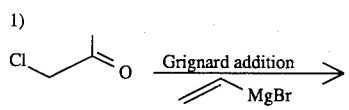

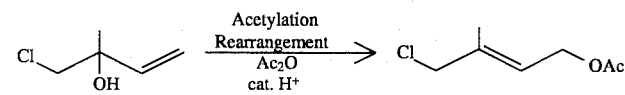

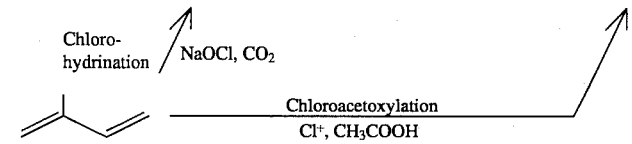

(U.S. Pat. No. 4,175,204; J. Org. Chem. 44, 1716 (1979))

This process is uneconomical because it uses expensive reagents such as p-toluenesulfonic acid. Further, the yield is at most 60% because the unstable halohydrin compound is produced under strongly acidic conditions and subjected to heating for hours. This process is environmentally unsuitable because of dimethyl sulfide responsible for the bad smell produced in the reaction.

2)

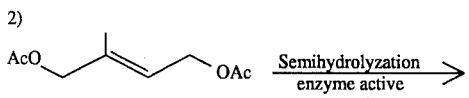

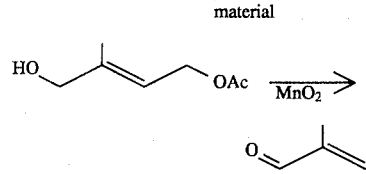

(see JP-A 58-198297)

This process uses a heavy metal such as manganese and requires the removal of the metal from the resulting desired compound 4-acyloxy-2-methyl-2-buten-1-al.

3)

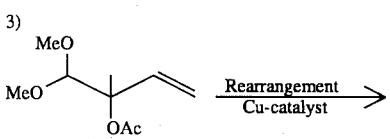

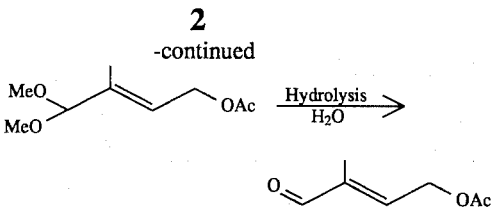

(see U.S. Pat. No. 4301084 (JP-A 55-55140))

4)

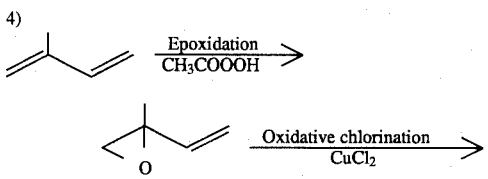

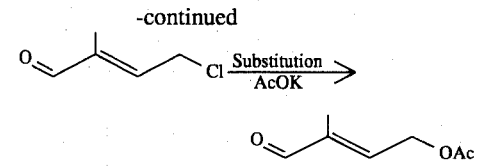

-continued

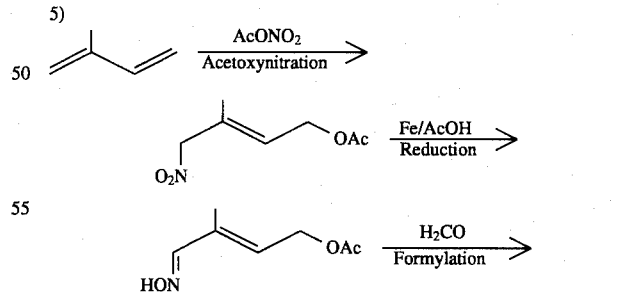

(see J. Org. Chem. 41, 1648 (1976))

5)

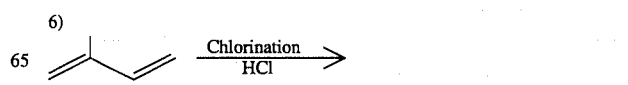

(see Synthesis, 649 (1977))

6)

-continued

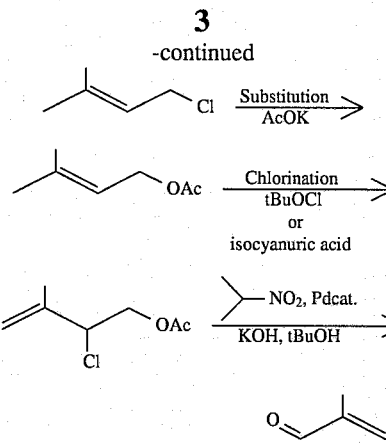

(see JP-A 61-194047)

Each of the above known processes for producing 4-acyloxy-2-methyl-2-buten-1-al is problematic and disadvantageous for an industrial process. For example, the processes require many reaction steps to obtain the desired compound from readily available industrial starting compounds, require severe reaction conditions, need reagents that must be handled with great care, involve unstable intermediate compounds, need expensive reagents, involve a low yield step, etc.

OBJECTS OF THE INVENTION

The main object of the present invention is to provide a novel process for producing 4-acyloxy-2-methyl-2-buten-1-al readily and in high yield from a readily available inexpensive industrial starting compound without using special reaction apparatuses and conditions.

This object as well as other objects and advantages of the present invention will become apparent to those skilled in the art from the following description.

SUMMARY OF THE INVENTION

The present inventors have intensively studied to accomplish the above objects. As a result, it has been found that aldehyde derivatives, particularly 4-acyloxy-2-methyl-2-buten-1-al can be obtained economically, readily, safely and in high yield by successively subjecting inexpensive and readily available isoprene to halohydrination, acylation optionally followed by rearrangement reaction, acyloxy-forming reaction, alcoholysis and oxidation. Thus, the present invention has been completed.

The present invention provides a process for producing a compound of the formula (III) (hereinafter sometimes referred to as the compound (III)):

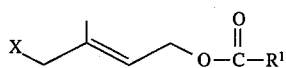 (III)

wherein R¹ is a saturated hydrocarbon group and X is halogen, which comprises acylating a compound of the formula (I) or (II) (hereinafter sometimes referred to as the compound (I) or (II)):

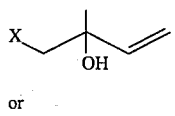 (I)

or

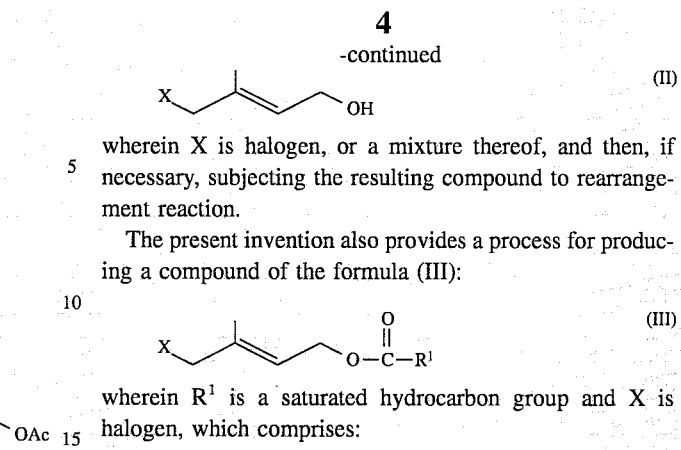 (II)

wherein X is halogen, or a mixture thereof, and then, if necessary, subjecting the resulting compound to rearrangement reaction.

The present invention also provides a process for producing a compound of the formula (III):

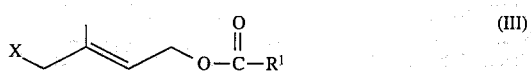 (III)

wherein R¹ is a saturated hydrocarbon group and X is halogen, which comprises:

subjecting isoprene to halohydrination to give a compound of the formula (I) or (II):

 (I)

or

 (II)

wherein X is halogen, or a mixture thereof;

acylating the compound of the formula (I) or (II) or a mixture thereof; and then, if necessary, subjecting the resulting compound to rearrangement reaction.

The present invention also provides a process for producing a compound of the formula (VI) (hereinafter sometimes referred to as the compound (VI)):

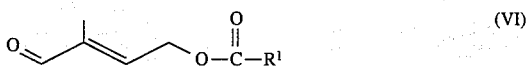 (VI)

wherein R¹ is a saturated hydrocarbon group, which comprises oxidizing a compound of the formula (V) (hereinafter sometimes referred to as the compound (V)):

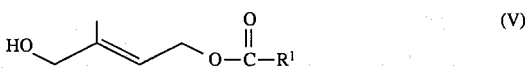 (V)

wherein R¹ is as defined above.

The present invention also provides a process for producing a compound of the formula (VI):

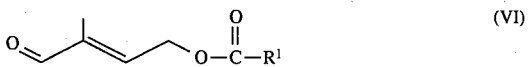 (VI)

wherein R¹ is a saturated hydrocarbon group, which comprises subjecting a compound of the formula (IV) (hereinafter sometimes referred to as the compound (IV)):

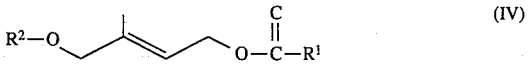 (IV)

wherein R¹ is a saturated hydrocarbon group and R² is an acyl group to alcoholysis to give a compound of the formula (V):

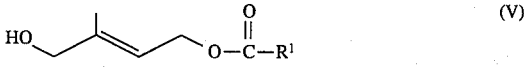 (V)

wherein R¹ as defined above, and oxidizing the compound of the formula (V).

The present invention also provides a process for producing a compound of the formula (VI):

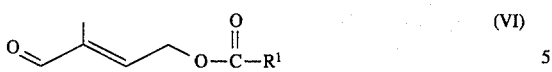

wherein $R^1$ is a saturated hydrocarbon group, which comprises:
subjecting a compound of the formula (III):

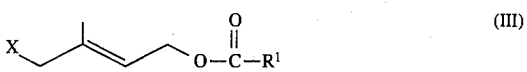

wherein $R^1$ as defined above and X is halogen to acyloxy-forming reaction to give a compound of the formula (IV):

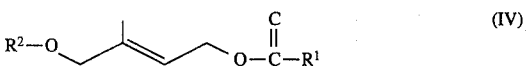

wherein $R^1$ is as defined above and $R^2$ is an acyl group;
subjecting the compound of the formula (IV) to alcoholysis to give a compound of the formula (V):

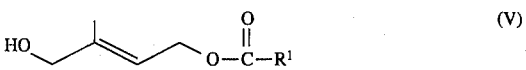

wherein $R^1$ as defined above; and
oxidizing the compound of the formula (V).

The present invention also provides a compound of the formula (IV-1) (hereinafter sometimes referred to as the compound (IV-1)):

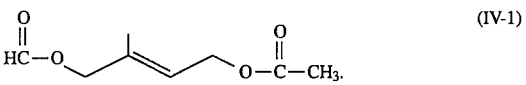

DETAILED DESCRIPTION OF THE INVENTION

Examples of the saturated hydrocarbon group represented by $R^1$ include saturated hydrocarbon groups having 1 to 20 carbon atoms, preferably alkyl groups (e.g., methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, eicosyl, etc.), cycloalkyl groups (e.g., cyclopropyl, cyclobutyl, cyclopentyl, cyclohexyl, etc.), etc. More preferred examples thereof include straight-chain or branched alkyl groups having 1 to 6 carbon atoms. In particular, methyl is preferred.

Examples of the acyl group represented by $R^2$ include acyl groups preferably derived from organic carboxylic acids such as acyl groups having 1 to 20 carbon atoms. Preferred examples of the acyl groups include formyl, alkylcarbonyl groups (i.e., alkanoyl groups), aryl-carbonyl groups (i.e., aroyl groups), aralkyl-carbonyl groups, etc. More preferred examples thereof include ($C_{1-6}$ alkyl)-carbonyl groups (e.g., acetyl, propionyl, butyryl, isobutyryl, valeryl, isovaleryl, pivaloyl, hexanoyl, etc.), ($C_{1-6}$ aryl)-carbonyl groups (e.g., benzoyl, 1- or 2-naphtoyl, etc.), ($C_{7-19}$ aralkyl)-carbonyl groups (e.g., benzylcarbonyl, 2-phenethylcarbonyl, 1- or 2-naphthylmethylcarbonyl, benzhydrylcarbonyl, etc.), etc. These acyl groups may be substituted with nitro, halogen (e.g., fluorine, chlorine, bromine, etc.), hydroxyl, oxo, carbamoyl, $C_{1-4}$ alkyl (e.g., methyl, ethyl, propyl, isopropyl, butyl, etc.), $C_{1-4}$ alkoxy (e.g., methoxy, ethoxy, propoxy, butoxy, etc.), optionally esterified carboxyl (e.g., methoxycarboxyl, ethoxycarboxyl, benzyloxycarboxyl, phenyloxycarboxyl, etc.), $C_{1-4}$ alkoxyimino optionally substituted with carboxyl (e.g., methoxyimino, ethoxy-imino, carboxymethoxyimino, 1-carboxy-1-methylethoxyimino, etc.), etc. Preferred examples of the acyl group include formyl and ($C_{1-6}$ alkyl)-carbonyl groups optionally substituted with carboxyl (e.g., acetyl, propionyl, butyryl, isobutyryl, valeryl, isovaleryl, pivaloyl, hexanoyl, carboxyacetyl, 3-carboxypropionyl, etc.). In particular, a formyl group is preferred.

Examples of the halogen represented by X include fluorine, chlorine, bromine, iodine, etc., preferably chlorine and bromine.

In a preferred process embodying the present invention, the compound (III) or (VI) are produced as follows.

Firstly, isoprene is subjected to halohydrination to give the compound (I) or (II) or a mixture thereof. The term "halohydrination" means a reaction giving a halohydrin. The halohydrination can normally be carried out by adding an alkaline metal salt (e.g., sodium salt, potassium salt, etc.) or alkaline earth metal salt (e.g., magnesium salt, potassium salt, etc.) of hypohalogenous acid to an aqueous suspension of isoprene. Preferably, salts of hypochlorous acid (e.g., sodium hypochlorite, potassium hypochlorite, magnesium hypochlorite, calcium hypochlorite, etc.) are used.

The halohydrination is preferably carried out at a pH of about 7 to about 9. Adjusting the reaction mixture to the pH region affords the halohydrin (i.e., the compound (I) or (II)) in high yield. The pH adjustment can readily be carried out by using a pH adjustor such as a strong acid (e.g., sulfuric acid, hydrochloric acid, phosphoric acid, nitric acid, etc.). Even when a strong acid is used as the pH adjustor to produce a halohydrin unstable in acidic conditions, the halohydrin can be obtained in such a high yield as at least 90%.

The reaction temperature is about $-10°$ C. to about $40°$ C., preferably about $0°$ C. to about $10°$ C. Preferably, isoprene is used in small excess relative to the halogenous acid, for example, in an amount of about 0.8 to about 3 mol, preferably about 1.2 to about 1.5 mol per mol of the hypohalogenous acid.

After completion of the reaction, the resulting halohydrin is extracted with an organic solvent. Examples of the organic solvent include hydrocarbons (e.g., benzene, toluene, etc.), halogenated hydrocarbons (e.g., 1,2-dichloroethane, dichloromethane, etc.), ethers (e.g., diethyl ether, isopropyl ether, etc.), acetic acid esters (e.g., ethyl acetate, isopropyl acetate, etc.), etc. The halohydrin may be purified by concentrating the extract by per se known methods and distillating the residue, or may be purified by column chromatography, etc. Alternatively, the concentrate can be used as it is in the next step, namely acetylation optionally followed by rearrangement reaction.

The halohydrin (i.e., the compound (I) or (II) or a mixture thereof) thus obtained is acylated and then, if necessary, subjected to rearrangement reaction to give the compound (III).

The acylation can normally be carried out by reacting the halohydrin with an acylating agent. The acylating agent to be used in this reaction is, for example, a carboxylic acid of the formula:

$$R^1\text{—COOH} \qquad \text{(VII)}$$

wherein $R^1$ is as defined above, or its reactive derivative having an activated carboxyl group. Examples of the reactive derivative having an activated carboxyl group are acid halides, acid anhydrides, activated amides, activated esters, activated thioesters, etc., each of which can be prepared by conventional methods. Examples of these reactive derivatives are as follows.

1) Acid halides:

Examples of the acid halides are acid chloride, acid bromide, etc.

2) Acid anhydrides:

Examples of the acid anhydrides are symmetrical acid anhydrides (e.g., $(R^1CO)_2O$ wherein $R^1$ is as defined above), mono-$C_{1-6}$ alkyl carbonic acid mixed anhydride, etc.

3) Activated amides:

Examples of the activated amides are amides formed by a carboxylic acid of the formula (VII) and pyrazole, imidazole, 4-substituted imidazole, dimethylpyrazole, benzotriazole, etc.

4) Activated esters:

Examples of the activated esters are methoxymethyl esters; benzotriazole esters; 4-nitrophenyl esters; 2,4-dinitrophenyl esters; trichlorophenyl esters; pentachlorophenyl esters; esters formed by carboxylic acids of the formula (VII) with 1-hydroxy-1H-2-pyridone, N-hydroxysuccinimide, N-hydroxyphtalimide, etc.

5) Activated thioesters:

Examples of the activated thioesters are thioesters formed by carboxylic acids of the formula (VII) and heterocyclic thiols such as 2-pyridylthiol, 2-benzothiazolylthiol, etc.

The acylating agents are preferably acid anhydrides, more preferably acetic anhydride. The amount of the acylating agent to be used is about 1 to about 1.5 mol, preferably about 1.05 to about 1.2 mol per mol of the halohydrin. Preferably, the acylation can be carried out in the presence of a catalyst. The catalyst may be the same as that used in the following rearrangement reaction. The amount of the catalyst to be used is about 0.01 to about 1 mol %, preferably about 0.1 to about 0.5 mol % based on the halohydrin. The reaction temperature is about 0° C. to about 60° C., preferably about 0° C. to about 30° C. This reaction may be carried out in any organic solvent which does not have a detrimental effect on the reaction. Examples of the organic solvent include halogenated hydrocarbons such as 1,2-dichloroethane, chloroform, etc.

After completion of the acylation, a catalyst is preferably added for rearrangement reaction. Specific examples of the catalyst include strong acids, Friedel-Crafts catalysts, cation-exchange resins, group VIII metal salts, etc. The strong acids include, for example, sulfuric acid, phosphoric acid, perchloric acid, trichloroacetic acid, etc. Friedel-Crafts catalysts include, for example, titanium tetrachloride, boron trifluoride, tin tetrachloride, aluminium trichloride, etc. The cation-exchange resins include, for example, Diaiion, Dowex, Amberlite, etc. The group VIII metal salts include, for example, chloride, nitrate, acetate of ruthenium, palladium, rhodium, platinum, or complex salts composed of these metals and triphenylphosphine, etc. Strong acids and group VIII metal salts are preferred. In particular, perchloric acid and palladium acetate are preferred.

The amount of the catalyst to be added at this time (i.e., rearrangement reaction) is about 0.1 to about 10 mol %, preferably about 1 to about 2 mol % based on the halohydrin. The temperature for the rearrangement reaction is about 0° C. to about 60° C., preferably about 10° C. to about 30° C. The time for the rearrangement reaction is about 1 to about 12 hours.

After completion of the rearrangement reaction, the haloacyl compound (i.e., the compound (III)) can be purified, for example, by washing the reaction mixture with water in an organic solvent-water system, distributing acetic acid and the catalyst to the aqueous layer to remove them, and concentrating the oil layer, followed by distillation. The haloacyl compound can also be purified by column chromatography. Alternatively, the concentrate may be used as it is in the next step.

Then, the resulting compound (III) is subjected to acyloxy-forming reaction to give a compound of the formula (IV). The term "acyloxy-forming reaction" means a reaction forming an acyloxy compound. The acyloxy-forming reaction is normally carried out using a metal carboxylate. Examples of the carboxylic acid include carboxylic acids corresponding to the desired acyloxy compounds, for example, represented by the formula: $R^2$—OH wherein $R^2$ is as defined above.

Examples of the metal carboxylate include alkaline metal (e.g., sodium, potassium, etc.) carboxylates, etc., preferably sodium formate. When metal formate is used, formyloxy-forming reaction can be carried out. The amount of the metal carboxylate is about 1 to about 5 mol, preferably about 1.5 to about 2 mol per mol of the compound (III).

In this reaction, the metal carboxylate may be used in powder form or in an aqueous solution thereof.

When the metal carboxylate is in a powder form, the compound (III) and the metal carboxylate powder are suspended in an organic solvent. The reaction temperature in this case is about 0° C. to about 80° C., preferably about 20° C. to about 60° C. This reaction may be carried out in an organic solvent. Any organic solvents which do not have an detrimental effect on the reaction can be used. Examples of the organic solvent include hydrocarbons (e.g., benzene, toluene, etc.), ethers (e.g., diethyl ether, etc.), halogenated hydrocarbons (e.g., 1,2-dichloroethane, dichloromethane, etc.), acetic acid esters (e.g., ethyl acetate, isopropyl acetate, etc.), amides (e.g., N,N-dimethylformamide, N,N-dimethylacetamide, haxamethylphosphoric triamide, etc.), etc. In particular, amides are preferred.

When the metal carboxylate is used in an aqueous solution thereof, the reaction is preferably carried out in two layers consisting of an aqueous layer and organic solvent layer homogeneously immiscible with water. The reaction temperature in this case is about 0° C. to about 80° C., preferably about 20° C. to about 60° C. Any organic solvent can be used as long as it is homogeneously immiscible with water. Examples of the organic solvent include hydrocarbons (e.g., benzene, toluene, etc.), halogenated hydrocarbons (e.g., 1,2-dichloroethane, dichloromethane, etc.), ethers (e.g., diethyl ether, etc.), acetic acid esters (e.g., ethyl acetate, isopropyl acetate, etc.), etc.

The above acyloxy-forming reaction may be carried out in the presence of a quaternary ammonium salt to speed up the reaction. The quaternary ammonium salt is not specifically limited and includes, for example, tetra-n-alkylammonium halides such as tetra-n-butylammonium iodide, tetra-n-pentylammonium bromide, tetraphenylammoniumchloride, etc. The amount of the quaternary ammonium salt is normally about 0.1 to about 20 mol %, preferably about 1 to about 5 mol % based on the compound (III).

The acyloxy compound (IV) thus obtained can be purified by washing it with water and evaporating the solvent for example, followed by distillation, etc. It can also be purified by column chromatography. The concentrate can be used as it is in the next step.

The alcoholysis of the compound (IV) can be carried out, for example, in an alcohol as a solvent in the presence of a catalyst. Examples of the catalyst include alkaline metal carbonates (e.g., sodium carbonate, potassium carbonate, lithium carbonate, etc.), alkaline metal bicarbonates (e.g., sodium bicarbonate, potassium bicarbonate, etc.), etc. In particular, alkaline metal carbonates are preferred, and sodium bicarbonate is more preferred. The amount of the catalyst to be used is about 0.1 to 20 mol %, preferably about 1 to 10 mol % based on the compound of the formula (IV). Examples of the alcohol include lower alcohol such as methanol, ethanol, propanol, etc. These alcohol can be used alone or as a mixture thereof. In particular, methanol is preferred. When methanol is used, methanolysis can be carried out. The alcohol is used in such an amount that the concentration of the compound (IV) is about 0.1 to about 3 mol/liter, preferably about 0.8 to about 1.2 mol/liter. As a solvent, a mixed solvent of an alcohol and an organic solvent other than an alcohol may be used. The reaction temperature is about 0° C. to about 60° C., preferably about 0° C. to about 30° C.

The allyl alcohol of the formula (V) thus obtained can be separated, for example, as follows. To the reaction mixture, an acid such as sulfuric acid, hydrochloric acid, acetic acid, formic acid, etc., can be added in an equivalent amount (mol) to the base used as the catalyst. Evaporation of the solvent under reduced pressure gives a compound of the formula (V) as the crude product. The crude product can be used as it is in the next step, or purified by distillation, column chromatography, etc.

Then, the compound of the formula (V) is oxidized to give the desired compound of the formula (VI). The oxidation can be carried out by conventional oxidation, for example, by bubbling air or oxygen into the reaction system in the presence of a catalyst (e.g., N-oxy radical compounds, cuprous chloride, etc.) in an organic solvent.

Examples of the N-oxy radical compound include 4-oxo-2,2,6,6-tetramethylpiperidinyl-1-oxy, 4-hydroxy-2,2,6,6-tetramethylpiperidinyl- 1-oxy,2,2,6,6-tetramethylpiperidinyl-1-oxy, etc. The amount of the catalyst to be used is about 1 to about 30 mol %, preferably about 2 to about 10 mol % based on the compound (V). The amount of the cuprous chloride to be used is about 1 to about 30 mol %, preferably about 3 to about 10 mol % based on the compound (V).

Any solvent can be used so long as it does not have a detrimental effect on the reaction. Examples of the solvent include amides such as N,N-dimethylformamide, N,N-dimethylacetamide, N-methylpyrrolidone, etc.

The reaction is carried out at about 0° C. to about 100° C., preferably about 30° C. to about 50° C. at atmospheric pressure or pressure, preferably at about 0 to about 20 kg/m$^2$. The volume of the oxygen or air to be bubbled into the reaction system varies with the pressure, and is normally about 0.001 to about 1.0 Nm$^3$, about 0.2 to 0.3 Nm$^3$ at atmospheric pressure.

The desired compound (VI) thus obtained can be purified by conventional methods, for example, by washing it with water in an organic solvent/water layer, followed by distillation under reduced pressure.

As described above, according to the present invention, there is provided a novel process for producing aldehyde derivatives, particularly, 4-acyloxy-2-methyl-2-buten- 1-al readily, economically, safely and in high yield from a readily available inexpensive industrial starting compound without using special reaction apparatuses, severe reaction conditions and dangerous reagents.

The following examples further illustrate the present invention in detail, but are not to be construed to limit the scope of the present invention. Each percentage (%) in Examples indicates w/w % unless otherwise stated.

EXAMPLE 1

Synthesis of isoprene chlorohydrin

95% isoprene (8.96 g, 125 mmol) and water (100 ml) were maintained at 0° C. in a 500 ml four neck flask. To this mixture were added 1N sulfuric acid (about 100 ml) and a 1 mol aqueous sodium hypochlorite solution (100 ml, 100 mmol) so that the pH of the reaction mixture was maintained at 7 to 9. During the addition, the reaction temperature was maintained at 0° C. to 5° C. The addition was completed after about 4 hours. The pH at the completion of the addition was adjusted to 6 to 7 with 1N sulfuric acid. The mixture was extracted with 1,2-dichloroethane (100 ml) three times. The extract was assayed by gas chromatography. Isoprene (2.05 g, 30.1 mmol) was recovered, and the 1,2-adduct (7.13 g, 59.1 mmol) and the 1,4-adduct (3.35 g, 27.8 mmol) were obtained. The reaction yield was 91.6%.

EXAMPLE 2

Synthesis of 4-acetoxy-2-methyl-1-chloro-2-butene

Acetic anhydride (9.32 g, 91.2 mmol, 1.05 equivalents) and a 60% aqueous perchloric acid solution (29.1 mg, 0.174 mmol, 0.2 mol %) were placed in a 100 ml four neck flask. Isoprene chlorohydrin (a mixture of 1,2-adduct and 1,4-adduct)(10.48 g, 86.9 mmol) was added so that the reaction temperature was maintained at 15° to 20° C. After stirring for 2 hours, a 60% aqueous perchloric acid solution (145.5 mg, 0.869 mmol, 1 mol %) was added. The mixture was stirred at room temperature for additional 2 hours. After completion of the reaction, water (50 ml) and 1,2-dichloroethane (50 ml) were added, and the mixture was washed with water. Then, the 1,2-dichloroethane layer was dried over anhydrous sodium sulfate. Evaporation of the 1,2-dichloroethane followed by distillation under reduced pressure (3–5 mmHg, 60°–65° C.) gave 4-acetoxy-2-methyl-1-chloro-2-butene (12.79 g, 78.6 mmol; Yield: 90.5%).

EXAMPLE 3

Synthesis of 4-acetoxy-2-methyl-2-buten-1-ol formate

4-Acetoxy-2-methyl-1-chloro-2-butene (8.13 g, 50 mmol) was dissolved in dimethylformamide (25 ml) and placed in a 100 ml four neck flask. To this were added sodium formate powder (6.80 g, 100 mmol, 2 equivalents) and tetra n-butylammonium bromide (0.81 g, 2.5 mmol, 5 mol %). The mixture was stirred at 40° C. for 24 hours under heating. After completion of the reaction, the reaction mixture was poured into ice-cooled water (about 30 ml) and extracted with ether (50 ml) three times. The extracted ether layer was dried over anhydrous sodium sulfate. Evaporation of the ether followed by purification by silica gel column chromatography (ethyl acetate-hexane (=1:3)) gave 4-acetoxy-2-methyl-2-buten-1-ol formate (8.18 g, 47.5 mmol; Yield: 95.0%).

$^1$H-NMR (CDCl$_3$): δ1.80 (d,3H), 2.12 (s,3H), 4.50–4.82 (m,4H), 5.72 (t,1H), 8.18 (s,1H).

EXAMPLE 4

Synthesis of 4-acetoxy-2-methyl-2-buten-1-ol

Sodium bicarbonate (0.40 g, 4.75 mmol, 10 mol %) was added to a solution of 4-acetoxy-2-methyl-2-buten-1-ol formate (8.18 g, 47.5 mmol) in methanol (40 ml). The mixture was stirred at room temperature for 2 hours. After completion of the reaction, most of the methanol was evaporated under reduced pressure. The resulting reaction mixture was poured into a mixture of ice-cooled water (20 ml) and ethyl acetate (100 ml). The pH of the aqueous layer was adjusted to 5 to 6 with 1N hydrochloric acid, and the ethyl acetate layer was separated. The aqueous layer was extracted with ethyl acetate (50 ml) twice. The ethyl acetate layers were combined and dried over anhydrous sodium sulfate. Evaporation of the ethyl acetate gave 4-acetoxy-2-methyl-2-buten-1-ol (6.69 g, 46.4 mmol; Yield: 97.7%) as an oil.

$^1$H-NMR (CDCl$_3$): δ; 1.82 (s,3H), 2.06 (s,3H), 2.61 (—OH,1H), 4.04 (s,2H), 4.65 (d,2H), 5.62 (t,1H).

EXAMPLE 5

Synthesis of 4-acetoxy-2-methyl-2-buten-1-al

To a solution of 4-acetoxy-2-methyl-2-buten-1-ol (6.69 g, 46.4 mmol) in dimethylformamide (40 ml) were added 2,2,6,6-tetramethyl-piperidine-1-oxy (0.39 g, 2.32 mmol, 5 mol %) and cuprous chloride (0.48 g, 4.64 mmol, 10 mol %). The mixture was subjected to reaction at 40° C. for 8 hours while bubbling oxygen at a rate of about 100 ml/min. After completion of the reaction, the reaction mixture was poured into ice-cooled water (30 ml) and extracted with ether (100 ml) three times. The extract was dried over anhydrous magnesium sulfate. Evaporation of the ether followed by purification by column chromatography (ethyl acetate-hexane (=1:3)) gave 4-acetoxy-2-methyl-2-buten-1-al (6.02 g, 42.3 mmol; Yield: 91.2%).

What is claimed is:

1. A process for producing a compound of the formula (III):

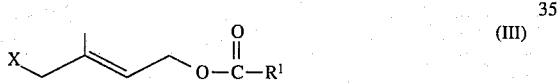
(III)

wherein R$^1$ is a saturated hydrocarbon group and X is halogen, which comprises:

subjecting isoprene to halohydrination carried out at a pH of about 5 to 9 to give a compound of the formula (I) or (II):

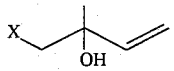
(I)

or

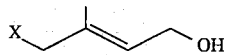
(II)

or a mixture thereof, wherein X is halogen;

acylating the compound of the formula (I) or (II) or a mixture thereof; and then, if necessary, subjecting the resulting compound to rearrangement to give the compound of formula (III).

2. A process according to claim 1, wherein R$^1$ is a saturated hydrocarbon group having 1 to 20 carbon atoms.

3. A process according to claim 1, wherein R$^1$ is a straight-chain or branched alkyl group having 1 to 6 carbon atoms.

4. A process according to claim 1, wherein the rearrangement reaction is carried out in the presence of a catalyst.

5. A process according to claim 4, wherein the catalyst is a strong acid, Friedel Crafts catalyst, cation-exchange resin or group VIII metal salt.

6. A process according to claim 4, wherein the catalyst is perchloric acid or palladium acetate.

7. A process according to claim 1, wherein the halohydrination is carried out at a pH of about 7 to 9.

8. A process for producing a compound of the formula (I) or (II):

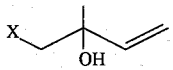
(I)

or

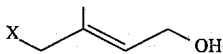
(II)

or a mixture thereof, wherein X is halogen; comprising subjecting isoprene to halohydrination carried out at a pH of about 5 to 9.

9. A process according to claim 8, wherein the halohydrination is carried out at a pH of about 7 to 9.

10. A process according to claim 1, wherein the halohydrination is carried out at a pH of about 6 to 9.

11. A process according to claim 8, wherein the halohydrination is carried out at a pH of about 6 to 9.

* * * * *